US006217541B1

United States Patent
Yu

(10) Patent No.: US 6,217,541 B1
(45) Date of Patent: Apr. 17, 2001

(54) BLOOD PUMP USING CROSS-FLOW PRINCIPLES

(75) Inventor: Long Sheng Yu, Carmichael, CA (US)

(73) Assignee: Kriton Medical, Inc., Sacramento, CA (US)

( * ) Notice: Subject to any disclaimer, the term of this patent is extended or adjusted under 35 U.S.C. 154(b) by 0 days.

(21) Appl. No.: 09/233,567

(22) Filed: Jan. 19, 1999

(51) Int. Cl.[7] ................................................... A61M 5/00
(52) U.S. Cl. ................................. 604/9; 604/151; 623/3; 415/900
(58) Field of Search ................................. 600/16; 623/3; 415/53.1–53.3, 900; 416/187; 417/420, 423.1, 423.4; 604/8, 9, 151, 6.11; 128/898

(56) References Cited

U.S. PATENT DOCUMENTS

| | | |
|---|---|---|
| 3,667,069 | 6/1972 | Blackshear et al. . |
| 4,173,981 * | 11/1979 | Mortensen ............................ 604/282 |
| 4,407,271 | 10/1983 | Schiff . |
| 4,589,822 * | 5/1986 | Clausen et al. ..................... 415/174.3 |
| 4,625,712 | 12/1986 | Wampler . |
| 4,688,998 * | 8/1987 | Olsen et al. ........................... 417/356 |
| 4,753,221 | 6/1988 | Kensey et al. . |
| 4,779,614 * | 10/1988 | Moise ..................................... 600/16 |
| 5,092,844 | 3/1992 | Schwartz et al. . |
| 5,282,849 * | 2/1994 | Kolff et al. . |
| 5,290,236 * | 3/1994 | Mathewson ............................ 604/131 |
| 5,344,443 * | 9/1994 | Palma et al. ............................... 623/3 |
| 5,385,581 * | 1/1995 | Bramm et al. . |
| 5,458,459 * | 10/1995 | Hubbard et al. ...................... 415/206 |
| 5,611,667 | 3/1997 | Nagamori et al. . |
| 5,685,700 * | 11/1997 | Izraelev .............................. 417/423.7 |
| 5,749,855 | 5/1998 | Reitan . |
| 5,810,758 * | 9/1998 | Yamazaki et al. ........................ 604/4 |
| 5,830,370 * | 11/1998 | Maloney, Jr. et al. ................ 210/780 |
| 5,882,339 * | 3/1999 | Beiser et al. .......................... 604/153 |
| 5,888,241 | 3/1999 | Jarvik . |
| 5,900,142 * | 5/1999 | Maloney, Jr. et al. . |
| 5,911,685 | 6/1999 | Siess et al. . |

OTHER PUBLICATIONS

Butler et al.: "Development of a 14 FR. Size Hemopump"; Annual International Conference of the IEEE Engineering in Medicine and Biology Society, vol. 12, No. 2, Nov. 1–4, 1990, pp. 735–736.

O.E. Balje, "Turbomachines", John Wiley & Sons, Inc., 1981 ISBN 0–271–06036–4, pp. 473–479.

* cited by examiner

Primary Examiner—Anhtuan T. Nguyen
Assistant Examiner—Jeremy Thissell
(74) Attorney, Agent, or Firm—George H. Gerstman; Seyfarth Shaw

(57) ABSTRACT

A blood pump is provided which comprises a cross-flow pump head having an elongated generally cylindrical housing portion. The housing portion defines a blood inlet port on a surface thereof and a blood outlet port on an opposite surface thereof. An impeller within the housing portion provides cross-flow of the blood from the inlet port around and/or across the rotational axis of the impeller to the outlet, and a motor is provided for driving the cross-flow pump head. The blood pump may be small enough to permit percutaneous insertion of the pump into a patient's blood vessel, and thus may be utilizable as a left ventricular assist device. To this end, a collapsible polymeric outflow tube is coupled to the blood flow outlet and is adapted for directing the blood from the left ventricle to the aorta through the aortic valve.

10 Claims, 4 Drawing Sheets

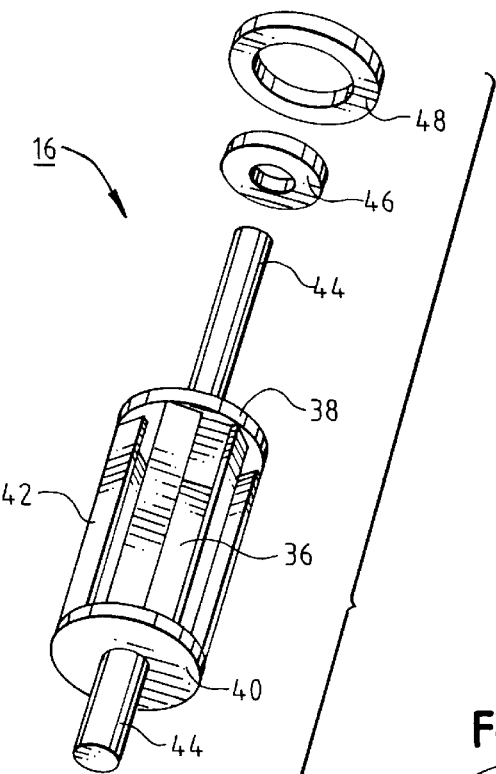
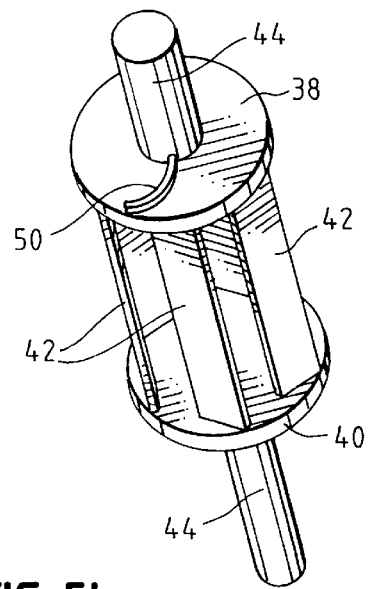
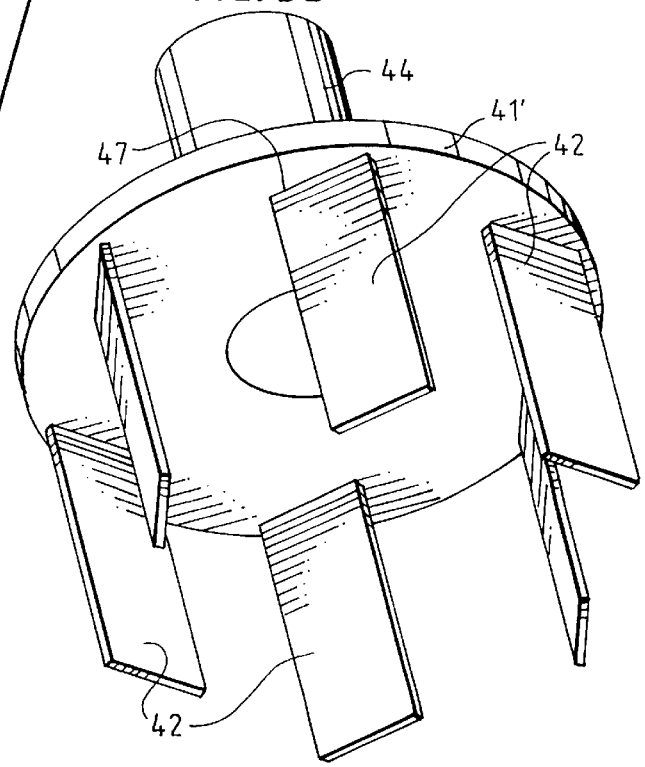

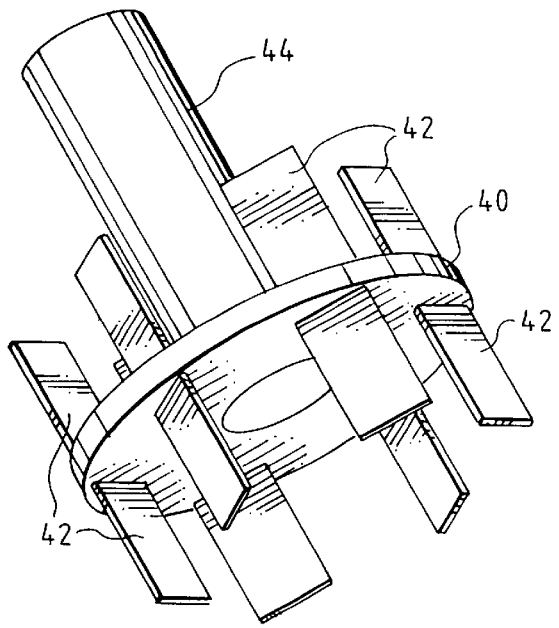
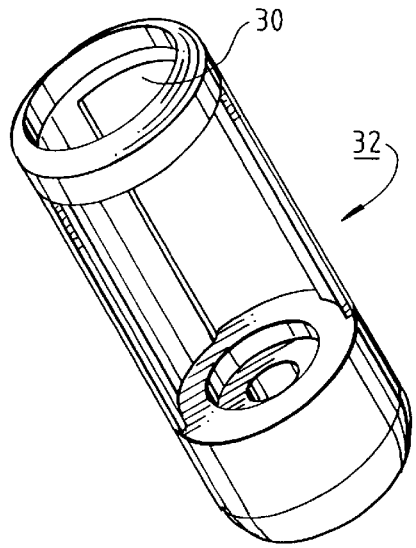
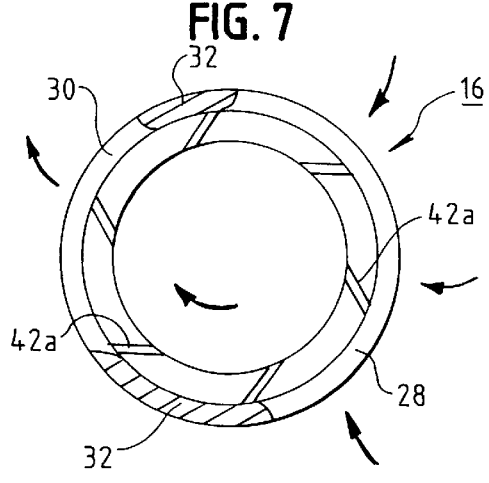
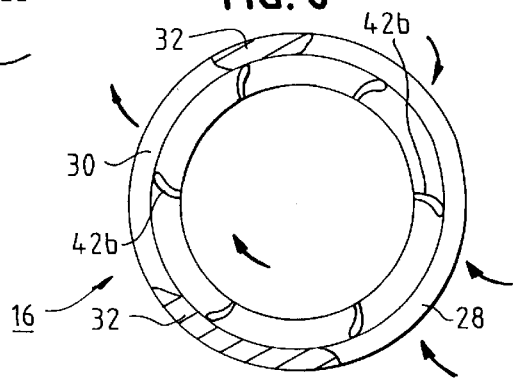

BLOOD PUMP USING CROSS-FLOW PRINCIPLES

FIELD OF THE INVENTION

The present invention concerns a novel blood pump, and more particularly, a blood pump that may be suitable as a ventricular assist device.

BACKGROUND OF THE INVENTION

Thousands of patients suffer cardiogenic shock following heart attacks or open heart surgery. These patients may benefit from mechanical circulatory support with a minimum output of 3 liters per minute. Many patients need temporary cardiac support during emergency transportation in an ambulance.

The need for a minimally invasive mechanical heart assist device has long been recognized. An ideal device would (1) have a cross-section of 12 French or less so that it could be adapted for insertion via a peripheral artery, such as the femoral artery (2) function intra-arterially and be inserted by a cardiologist without support from a surgeon and, (3) be capable of providing at least 3 liters per minute of flow at systemic pressures without a contribution from the native left ventricle. The intra-aortic balloon pump (IABP) has been used for years and is the industry standard because it is easy to insert and does not require surgery. It is readily inserted into the femoral artery by the cardiologist, but it has limited pumping capacity and can only be used for a patient who has some residual cardiac function. The flow of the IABP is limited to approximately 1.5 liters per minute to 2.0 liters per minute and is dependent upon synchronization with a left ventricle which must have some residual function.

There have been efforts to provide a temporary, minimally invasive pump for patients which require more cardiac output than can be provided by an IABP. The Hemopump is an axial flow blood pump which meets the criteria for blood flow (approximately 5 liters per minute) but it is too large (14 to 22 French) for easy insertion by a cardiologist. Although smaller versions of the Hemopump could be built, physics limits the flow because as the pump becomes smaller, the inlet area decreases. Losses in the pump increase in a rapid, non-linear manner as the inlet area decreases. To compensate for these rapidly increasing losses, the rotor speed must be increased exponentially. Although adequate flow may be achieved, hemolysis increases to unacceptable levels.

Thus the engineer faces theoretical and technical difficulties to make a traditional propeller pump or centrifugal pump with the diameter less than 4.0 mm and a flow of at least 3 liters per minute. One way to circumvent the physical limitations imposed by a decreasing inlet area is to make the pump expandable. In this way, inlet losses and shaft speed can be minimized since large areas can be achieved after the pump is inserted. Cable driven axial flow blood pumps have been described which use a hinged propeller that deploys after insertion into the arterial system. However, hemolysis has limited the adaptation of this concept as a clinical device. Other concepts for pumps that expand or deploy after insertion have been proposed. However, these miniature expandable pumps are challenging to manufacture and reliable mechanisms may be difficult to achieve.

The Hemopump and expandable pumps have constrained pump design by dictating that the inlet area must be located in a plane perpendicular to the axis of rotation. Consequently, an increase in the inlet area will also increase the diameter of the pump.

It is, therefore, an object of the present invention to achieve the benefits of a large inlet area without the necessity for enlarging the inlet diameter or making the blood pump expandable.

It is another object of the present invention to provide a blood pump which provides low inlet and outlet losses while maintaining a small diameter and without the need for an expandable mechanism.

A still further object of the present invention is to provide a blood pump that obviates the problems discussed above that are concomitant with prior art blood pumps.

A further object of the invention is to provide a blood pump having a 3 liter per minute or greater flow and having a diameter that is small enough to permit percutaneous insertion of the pump into a patient's blood vessel.

Another object of the invention is to provide a blood pump that is relatively simple in construction and relatively easy to manufacture.

Other objects and advantages of the present invention will become apparent as the description proceeds.

SUMMARY OF THE INVENTION

Cross-flow principles have been used in cross-flow air blowers. I have discovered that cross-flow air blower principles can be used effectively for a blood pump head.

In accordance with the present invention, a blood pump is provided which comprises a pump head having a cross-flow configuration. As used herein, a "cross-flow configuration" utilizes a housing in which an inlet is defined on a side of the housing and an outlet is defined on a side of the housing, with the flow from the inlet to the outlet being around and/or across the rotational axis of an impeller within the housing. The flow between the inlet and the outlet is preferably but not necessarily in a direction that is generally perpendicular to the rotational axis of the impeller.

In the illustrative embodiment of the present invention, the blood pump head has an elongated housing portion. The housing portion defines a blood inlet port on a surface thereof and a blood outlet port on a surface thereof. An impeller is located within the housing portion for providing cross-flow of the blood from the inlet port to the outlet port. A motor is provided for driving the cross-flow pump head.

In the illustrative embodiment, the blood inlet port and the blood outlet port have rectangular configurations. The blood inlet port is larger than the blood outlet port and the blood inlet port and blood outlet ports are defined on opposite surfaces.

In the illustrative embodiment, the housing portion is generally cylindrical and the blood inlet port defines an arc between 80° and 180° and the blood outlet port defines an arc less than 80°. The impeller has an axial length that is at least 2 times its diameter and the impeller has blades which rotate tangentially to the cylindrical planes that define the inlet and outlet ports.

In one embodiment, the impeller comprises a squirrel cage configuration. The impeller has a plurality of blades having a forward angle from 0° to 80° and a pair of axially spaced shrouds. The axial ends of the blades are attached to the axially spaced shrouds.

In that embodiment, the impeller has coaxial shafts extending outwardly from the shrouds. Bearings are provided for supporting the coaxial shafts within the housing. A wiper comprising either a ridge or a groove on an outside surface of a shroud is provided to aid in moving the blood around a shaft, to minimize the likelihood of thrombus deposition.

In another embodiment, instead of axially spaced shrouds, one shroud is located intermediate of the blades. In a further embodiment, one shroud is located only on one end of the blades. In one embodiment, the impeller shaft is magnetically coupled to the motor. In another embodiment, the motor is coupled to the impeller shaft via a flexible shaft and the motor is an air motor.

In one embodiment, the blood pump has an outer dimension that is small enough to permit percutaneous insertion of the pump into a patient's blood vessel. A collapsible polymeric outflow tube is provided and is coupled to the blood flow outlet of the pump and is adapted for directing the blood from the left ventricle of the patient to the aorta through the aortic valve.

In accordance with the present invention, a method is provided for pumping blood. The method comprises the steps of providing a cross-flow pump head having an elongated housing portion defining a blood inlet port on a surface thereof and a blood outlet port on a surface thereof; providing an impeller within said housing portion for providing cross-flow of the blood from the inlet port to the outlet port; and driving the cross-flow pump head with a motor to rotate the impeller and accelerate the blood from the inlet port within the housing portion.

A more detailed explanation of the invention is provided in the following description and claims, and is illustrated in the accompanying drawings.

BRIEF DESCRIPTION OF THE DRAWING

FIG. 4 is an exploded view of the pump head of FIG. 3.

FIG. 5a is a perspective view of an impeller constructed in accordance with one embodiment of the present invention.

FIG. 5b is a perspective view of an impeller constructed in accordance with another embodiment of the present invention.

FIG. 5c is a perspective view of an impeller constructed in accordance with a further embodiment of the present invention.

FIG. 6 is a perspective view of a pump housing constructed in accordance with the principles of the present invention.

FIG. 7 is a cross-sectional view of the housing and one form of impeller blades of the blood pump of FIGS. 3–6.

FIG. 8 is a cross-sectional view of the housing and another form of impeller blades of the blood pump of FIGS. 3–6.

DETAILED DESCRIPTION OF THE ILLUSTRATIVE EMBODIMENT

Figure 1:
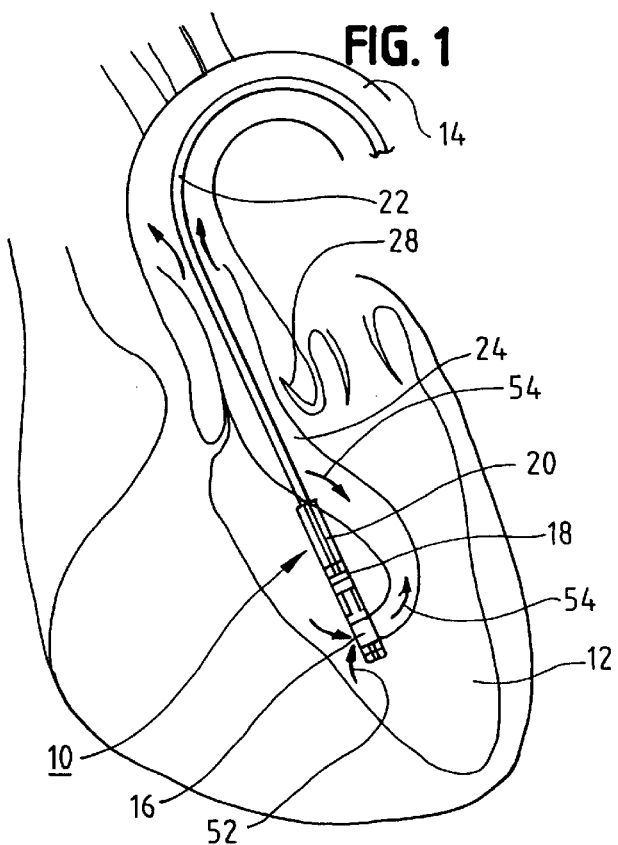
FIG. 1 is a diagrammatic view of a blood pump constructed in accordance with the principles of the present invention, with its drive motor located inside the left ventricle of a patient.

Referring to FIG. 1, a blood pump 10 is shown therein within a patient's left ventricle 12 and aorta 14. Blood pump 10 comprises a generally cylindrical pump head 16, magnetic coupling 18, a motor 20 that is either air driven or electrically driven, and a drive line 22 that is an air driven line for an air driven motor or is an electric line for an electrically driven motor. Pump head 16 is small enough to be insertable into a patient's artery, with head 16 having a diameter of between 3 French and 12 French. As a specific example although no limitation is intended, it is preferred that the diameter of pump head 16 be about 10–12 French and that the length be about one inch.

Figure 1A:
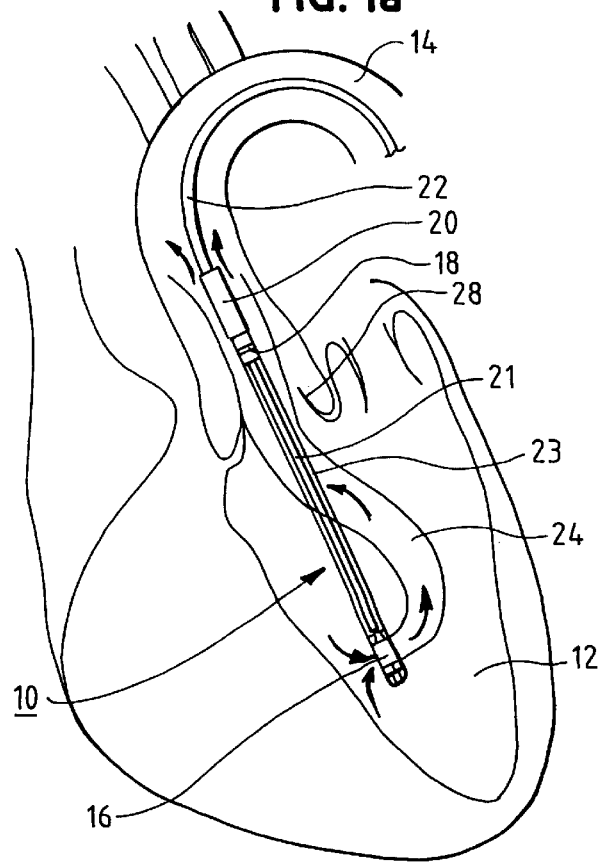
FIG. 1a is a diagrammatic view of a blood pump constructed in accordance with another form of the present invention, with its drive motor located inside the aorta of a patient.

In FIG. 1, both pump head 16 and motor 20 are located within the patient's left ventricle. Referring now to FIG. 1a, another form of the invention is shown in which the pump head 16 is located within the patient's left ventricle while the motor 20 is located in the patient's aorta. In FIG. 1a, pump head 16 is coupled to motor 20 by means of a flexible shaft 21 surrounded by shaft jacket 23 and magnetic coupling 18.

One of the benefits of using flexible-driven shaft 21 and locating the motor 20 outside of the ventricle is that it permits pump head 16 to be increased in length. In contrast to prior art blood pumps, in which greater output generally required greater radial dimension of the pump, by using a cross-flow pump in accordance with the present invention in order to achieve greater output, the length of the impeller and housing is increased and the need to provide a greater radial dimension is obviated.

Figure 2:
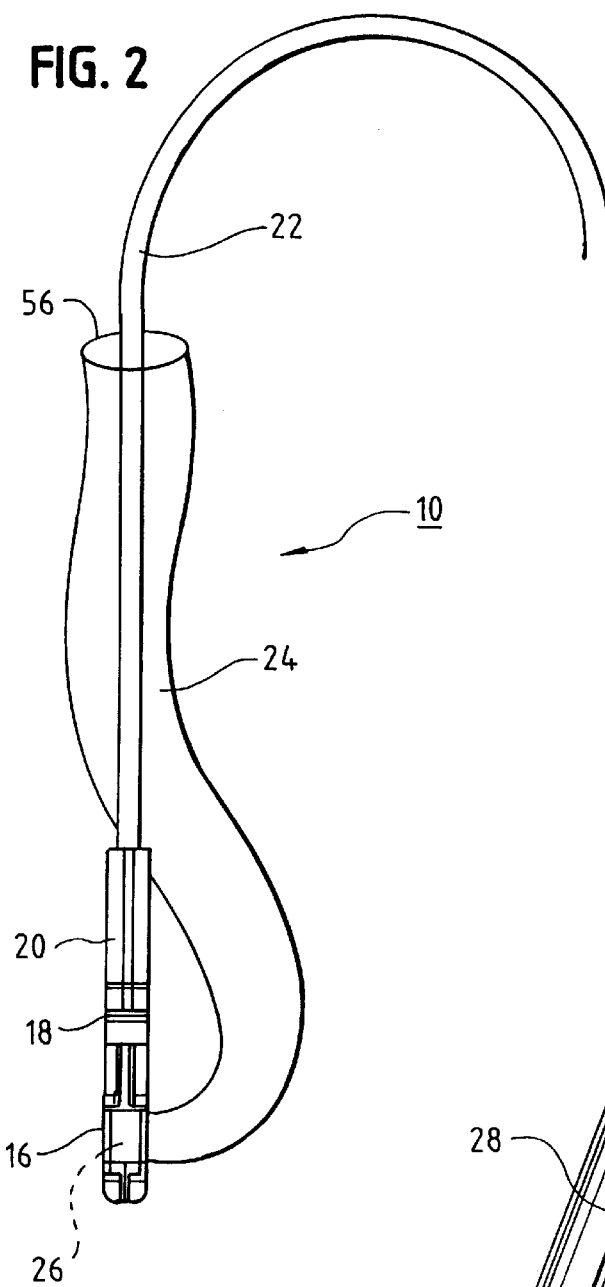
FIG. 2 is a diagrammatic view of a blood pump constructed in accordance with the principles of the present invention.

As shown more clearly in FIG. 2, a collapsible polymeric diffuser tube 24 is connected to the outlet 26 of pump head 16 for guiding the blood from the pump. The collapsible diffuser tube 24 attaches to the wall of the housing discharge opening 26. The diffuser tube 24 is of a sufficient length to transport blood from the left ventricle into the supravalvular aorta. The cross-sectional area of the collapsible diffuser tube 24 increases gradually as illustrated in FIG. 2, and can be much larger than the initial diameter of the pump, which may be only 4.0 mm.

As illustrated in FIG. 1, diffuser tube 24 extends into the aorta through the aortic valve 28. When the heart is pumping, the aortic valve 28 will be closed on the outside of the diffuser tube 24, preventing backward flow.

Figure 3:
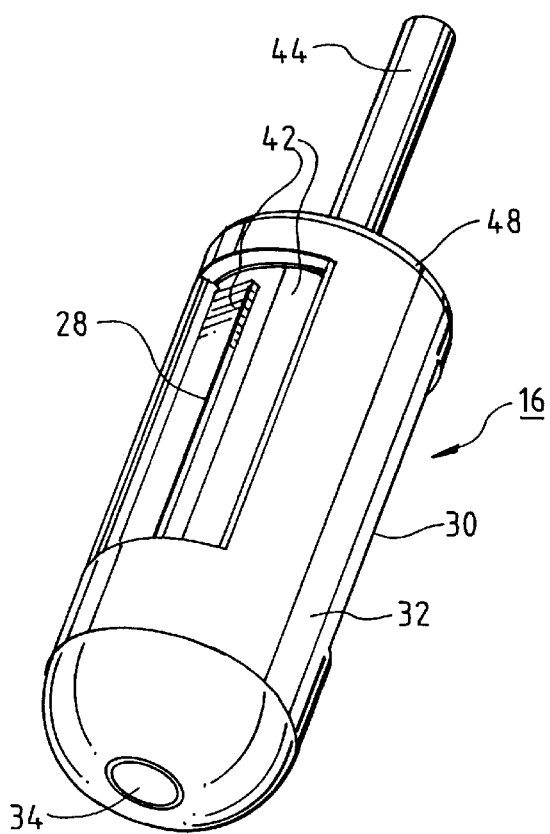
FIG. 3 is a perspective view of the head of a blood pump constructed in accordance with the principles of the present invention.

The pump head 16 is shown in more detail in FIG. 3. Referring to FIG. 3, the pump head comprises an elongated generally cylindrical housing 32 and forms a cross-flow pump. To this end, pump housing 32 defines an inlet port 28 and an outlet port 30, both of which are preferably rectangular in shape. The inlet port 28 is substantially larger than the outlet port 30. Although no limitation is intended, as an example the inlet port covers an arc on the pump head 16 of from 80° to 180° and the outlet port covers an arc of less than 80°.

Referring to FIG. 4, which is an exploded view of the pump head 16 of FIG. 3, it can be seen that the pump housing 32 also defines an opening 34 which permits blood to flow into the gap of a sliding bearing to lubricate the bearing. As illustrated in FIG. 4, the inlet opening 28 is on the opposite surface from outlet port 30, although other configurations may be acceptable.

Within the pump head housing 32 there is provided an impeller 36 which includes a pair of spaced shrouds 38, 40 and impeller blades 42 which extend axially and are connected at their ends to the insides of shrouds 38 and 40. Coaxial shafts 44 extend from the ends of shrouds 38 and 40 and a pair of composite sliding bearings 46 are provided for radial and axial support of the impeller. Coaxial shafts 44 may be a single, unitary shaft if desired, extending axially through the center of the impeller. A pump cover 48 is provided. The impeller blades 42 extend at a forward angle which may range from 0° to 80°.

Another view of the impeller 36 is illustrated in FIG. 5a. Referring to FIG. 5, it can be seen that a wiper 50 is provided on the impeller shroud 38. The wiper may be a single groove or a single ridge on the side of the shroud. When the impeller rotates, radial blood movement is produced in the gap between the shroud 38 and the housing 32. The blood will be washed around the shaft 44 to minimize the likelihood of thrombus deposition.

Another form of the impeller 36 is illustrated in FIG. 5b. In this form of the invention, a single shroud 40 is utilized on only one side of the blades 42 and thus the ends 47 of blades 42 are attached to the inside surface of the single shroud 40.

In FIG. 5c, a single shroud 40 is utilized and is located intermediate the ends of blades 42. In the FIG. 5c embodiment, the upper portion of blades 42 are equal to the lower portions of blades 42, although it is understood that it may be desirable for the upper and lower portions of the blades 42 to be unequal in length with respect to shroud 40.

FIG. 6 is another view of the pump housing 32. This view more clearly shows the pump outlet port 30 as viewed through the pump inlet port.

In FIG. 7 a cross-sectional view of the pump head is shown with impeller blades 42a that have a flat shape. It is preferred that there be between two to sixteen impeller blades and it is also preferred that the impeller blades 42b be curved, as illustrated in FIG. 8. In FIGS. 7 and 8, a blood flow path through the pump head is illustrated. It can be seen that the impeller blades rotate tangentially to the cylindrical planes that define the inlet and outlet ports 28, 30.

In using the blood pump of the present invention, the soft collapsible diffuser tube 24 is collapsed about the cross-flow pump. The cross-flow pump with its collapsed diffuser tube are introduced through the femoral artery, via an appropriate guiding catheter, so that the pump is positioned in the patient's left ventricle as illustrated in FIG. 1. The catheter is then removed and line 22 is coupled to a suitable source of air or current, depending on whether an air motor or electric motor is utilized. Blood enters the pump as shown by the arrow 52 in FIG. 1, through the cross-flow pump and through the tube 24 as indicated by arrows 54, to exit from the outlet 56 (FIG. 2) of diffuser tube 24 in the aorta. The initial pumping of the blood will enable the soft, collapsed diffuser tube 24 to expand to its fully opened characteristic as illustrated in FIGS. 1 and 2.

Alternatively, in using the blood pump of the present invention, the cross-flow pump with its collapsed diffuser tube are introduced through the femoral artery without using a guiding catheter.

It can be seen that a novel blood pump has been illustrated and described for providing low inlet and outlet losses while maintaining a small diameter and without requiring an expandable mechanism.

Although illustrative embodiments of the invention have been shown and described, it is to be understood that various modifications and substitutions may be made by those skilled in the art without departing from the novel spirit and scope of the present invention.

What is claimed is:

1. A method for pumping blood, which comprises the steps of:

providing a cross-flow pump head having a housing portion defining a blood inlet port on a surface thereof and a blood outlet port on a surface thereof;

providing an impeller, having impeller blades which rotate about a rotational axis, within said housing intermediate said blood inlet port and said blood outlet port for providing radial blood movement from said inlet port, through the impeller blades and across said rotational axis to the outlet port;

inserting the pump head into a patient's blood vessel; and driving the cross-flow pump head with a motor to rotate the impeller and accelerate the blood from the inlet port and through the impeller blades within the housing portion.

2. A method as defined in claim 1, including the step of coupling the pump head to the patient's heart to provide a cardiac assist device.

3. A method as defined in claim 2, including the step of providing a collapsible polymeric outflow tube coupled to the blood flow outlet; and directing the blood from the patient's left ventricle to the patient's aorta through the aortic valve.

4. A method as defined in claim 2, including the step of positioning both the pump head and the motor within the patient's ventricle.

5. A method as defined in claim 2, including the step of positioning the pump head in the patient's ventricle with the motor being located outside of the patient's ventricle.

6. A method for assisting a patient's heart, comprising the steps of:

providing a cross-flow pump head having a housing portion defining a blood inlet port on a surface thereof and a blood outlet port on a surface thereof;

introducing via the patient's arteries said cross-flow pump head having within said housing portion an impeller having an impeller blades which rotate about a rotational axis, with said impeller being located within said housing intermediate said blood inlet port and said blood outlet port for providing radial blood movement from said inlet port, through the impeller blades and across said rotational axis to the outlet port, and a motor for driving said cross-flow pump head;

coupling said cross-flow pump head to the patient's heart; and driving the cross-flow pump head with a motor to rotate the impeller and accelerate the blood from the inlet port and through the impeller blades within the housing portion.

7. A method as defined in claim 6, including the step of providing an outflow tube coupled to said blood flow outlet for directing the blood from the patient's left ventricle to the patient's aorta through the aortic valve.

8. A method for assisting a patient's heart, comprising the steps of:

inserting a catheter into a patient's artery;

introducing through the catheter a cross-flow pump including (a) a cross-flow pump head having a housing portion defining a blood inlet port on a surface thereof and a blood outlet port on a surface thereof, (b) an impeller having impeller blades which rotate about a rotational axis, said impeller located within said housing intermediate said blood inlet port and said blood outlet port for providing radial blood movement from said inlet port, through the impeller blades and across said rotational axis to the outlet port, (c) a motor for driving the cross-flow pump head, and (d) a collapsed outflow tube coupled to the blood flow outlet;

locating the cross-flow pump head in the patient's ventricle with said outflow tube extending into the patient's aorta through the aortic valve;

removing a catheter; and energizing the motor to rotate the impeller and accelerate the blood from the inlet port and through the impeller blades within the housing portion whereby the blood is pumped from the left ventricle to the aorta.

9. A method as defined in claim 8, including the step of positioning both the pump head and the motor within the patient's ventricle.

10. A method as defined in claim 8, including the step of positioning the pump head in the patient's ventricle with the motor being located outside of the patient's ventricle.

* * * * *